United States Patent [19]

Keene et al.

[11] Patent Number: 4,762,789
[45] Date of Patent: Aug. 9, 1988

[54] SERODIAGNOSTIC REAGENT FOR ENTAMOEBA HISTOLYTICA

[75] Inventors: William E. Keene, Berkeley; James H. McKerrow, San Francisco, both of Calif.

[73] Assignee: The University of California, Berkeley, Calif.

[21] Appl. No.: 819,892

[22] Filed: Jan. 16, 1986

[51] Int. Cl.[4] .................. C12N 9/50; C12N 15/00; C12Q 1/00; G01N 33/54
[52] U.S. Cl. .................................. 435/219; 435/4; 435/7; 435/172.3; 935/14
[58] Field of Search ............................ 435/219, 4, 7

[56] References Cited

PUBLICATIONS

Avila, E. E., Sanchez-Garza, M., and Calderon, J., 1985. Entamoeba histolytica and E. invadens: Sulfhydryl-dependent proteolytic activity. J. Protozool. 32:163–166.
Feingold, C., Bracha, R., Wexler, A., and Mirelman, D., 1985. Isolation, purification, and partial characterization of an enterotoxin from extracts of Entamoeba histolytica trophozoites. Infection and Immunity 48:211–218.
Gadasi, H., and Kessler, E., 1983. Correlation of virulence and collagenolytic activity in Entamoeba histolytica. Infection and Immunity 39:528–531.
Gadasi, H., and Kobiler, D., 1983. Entamoeba histolytica: correlation between virulence and content of proteolytic enzymes. Exp. Parasitol. 55:105–110.
Keene, W. E., and J. H. McKerrow, 1985. Isolation and characterization of the neutral thiol proteinase of virulent Entamoeba histolytica. Fed. Proc. Abstracts 44:1335. Abstract No. 5406.
Lushbaugh, W. B., Hofbauer, A. F., Kairalla, A. A., Cantey, J. R., and Pittman, F. E., 1984. Relationship of cytotoxins of axenically cultivated Entamoeba histolytica to virulence. Gastroenterol. 86:1488–1495.
Lushbaugh, W. B., Hofbauer, A. F., and Pittman, F. E., 1985. Entamoeba histolytica: Purification of cathepsin B. Exp. Parasitol. 59:328–336.
McGowan, K., Deneke, C. F., Thorne, G. M., and Gorbach, S. L., 1982. Entamoeba histolytica cytotoxin: Purification, Characterization, Strain Virulence, and Protease Activity. J. Infect. Dis. 146:616–625.
McKerrow, J. H., S. Pino-Heiss, R. L. Lindquist, and Z. Werb, 1985. Purification and characterization of an elastinolytic proteinase secreted by cercariae of Schistosoma mansoni. J. Biol. Chem. 260:3703–3707.
McLaughlin, J., and Faubert, G., 1977. Partial purification and some properties of a neutral sulfydryl and an acid proteinase from Entamoeba histolytica. Can. J. Microbiol. 23:420–425.
Munoz, M. A., Calderon, J., and Rojkind, M., 1982. The collagenase of Entamoeba histolytica. J. Exp. Med. 155:42–51.
Munoz, M.d.L.M., Rojkind, M., Calderon, J., Tanimoto, M., Arias-Negrete, S., and Martinez-Palomo, A., 1984. Entamoeba histolytica: Collagenolytic activity and virulence. J. Protozool. 31:468–470.
Scholze, H., and Werries, E., 1984. A weakly acidic protease has a powerful proteolytic activity in Entamoeba histolytica. Mol. Biochem. Parasitol. 11:293–300.

Primary Examiner—Lionel M. Shapiro
Attorney, Agent, or Firm—Fitch, Even, Tabin & Flannery

[57] ABSTRACT

The present invention is a composition of matter composed essentially of a purified homogeneous thiol proteinase secreted by Entamoeba histolytica trophozoites. In purified homogeneous form the neutral thiol proteinase has a subunit molecular weight of about $56,000 \pm 4,000$, a neutral pH optimum, and an isoelectric point of about 6. The purified neutral thiol proteinase of the present invention can be obtained by using anion exchange and chromatofocusing Fast Protein Liquid Chromatography (FPLC) to purify the major neutral proteinase from secretions of axenically cultured Entamoeba histolytica trophozoites.

The homogeneous neutral thiol proteinase of the present invention is immunogenic. It is useful as a serodiagnostic reagent for identifying the presence of antibodies in the sera of individuals exposed to Entamoeba histolytica trophozoites. The purified homogeneous enzyme can be used in ELISA assays or in other standard immunoassays.

3 Claims, 5 Drawing Sheets

SERODIAGNOSTIC REAGENT FOR ENTAMOEBA HISTOLYTICA

FIELD OF THE INVENTION

This invention relates to a homogeneous proteinaceous composition. More specifically, this invention relates to a purified thiol proteinase secreted by trophozoites of the human parasite *Entamoeba histolytica*. In isolated, homogeneous form, the *Entamoeba histolytica* thiol proteinase is immunogenic and useful as a serodiagnostic reagent for detecting the presence of antibodies to the protozoan parasite known to cause amebiasis.

BACKGROUND OF THE INVENTION

Amebiasis is defined as infection with *Entamoeba histolytica*. While the majority of infections are asymptomatic, intestinal manifestations may include dysentery and colitis. Most amebiasis-associated mortality stems from extra-intestinal infection, which results from invasion of the bowel wall and subsequent spread through the body. See Krogstad, et al. (1978). Amebiasis is one of the world's great health problems, especially in third world countries. It is also a disease of western countries, particularly of travelers, institutionalized persons, and homosexual males.

An amebic infection is usually acquired by the ingestion of food or water contaminated with cysts of *Entamoeba histolytica*. Sexual transmission has also been reported among homosexual males. Not surprisingly, amebiasis is a common complicating infection in AIDS patients.

At the present time diagnosis of amebiasis usually depends upon recognition of *Entamoeba histolytica* trophozoites or cysts in stool specimens. Such recognition is technically difficult and time consuming. Thus the test is costly, and unreliable unless run by highly trained technical personnel. Serodiagnostic tests are a valuable supplement to stool smear tests as a means of diagnosing amebiasis, particularly of the more serious invasive infections. The serodiagnostic tests can be run more quickly than the smear tests, and they can be run by less technically trained personnel. Several serodiagnostic tests are now available that can help identify those individuals who have been infected with *Entamoeba histolytica*. These tests include indirect hemagglutination, gel diffusion precipitation, and ELISA tests. Unfortunately, all of these serodiagnostic tests share the disadvantage of relying on crude extracts of *Entamoeba histolytica* as a source of the antigen. The crude extracts of *Entamoeba histolytica* are really a complex mixture of poorly defined antigens. As a result the individual epitopes and antigenic moieties cannot be identified or produced readily in large amounts. Defined antigens, which can be produced readily in large amounts, are necessary before a more specific serodiagnostic test can be devised. Such a specific serodiagnostic test would make it possible to more accurately detect the presence of antibodies to *Entamoeba histolytica* in the sera of patients with amebiasis. Thus there is a need for an immunogenic moiety or antigenic reagent that is specific to *Entamoeba histolytica* and which can be prepared easily in large amounts. It is an object of the present invention to provide an immunogenic compound that will function as a serodiagnostic reagent for amediasis tests. It is a further object of the present invention to provide an immunogenic reagent that is specific to *Entamoeba histolytica* and which can be prepared easily in large amounts.

DRAWINGS

DETAILED DESCRIPTION OF THE FIGURES

Figure 1:
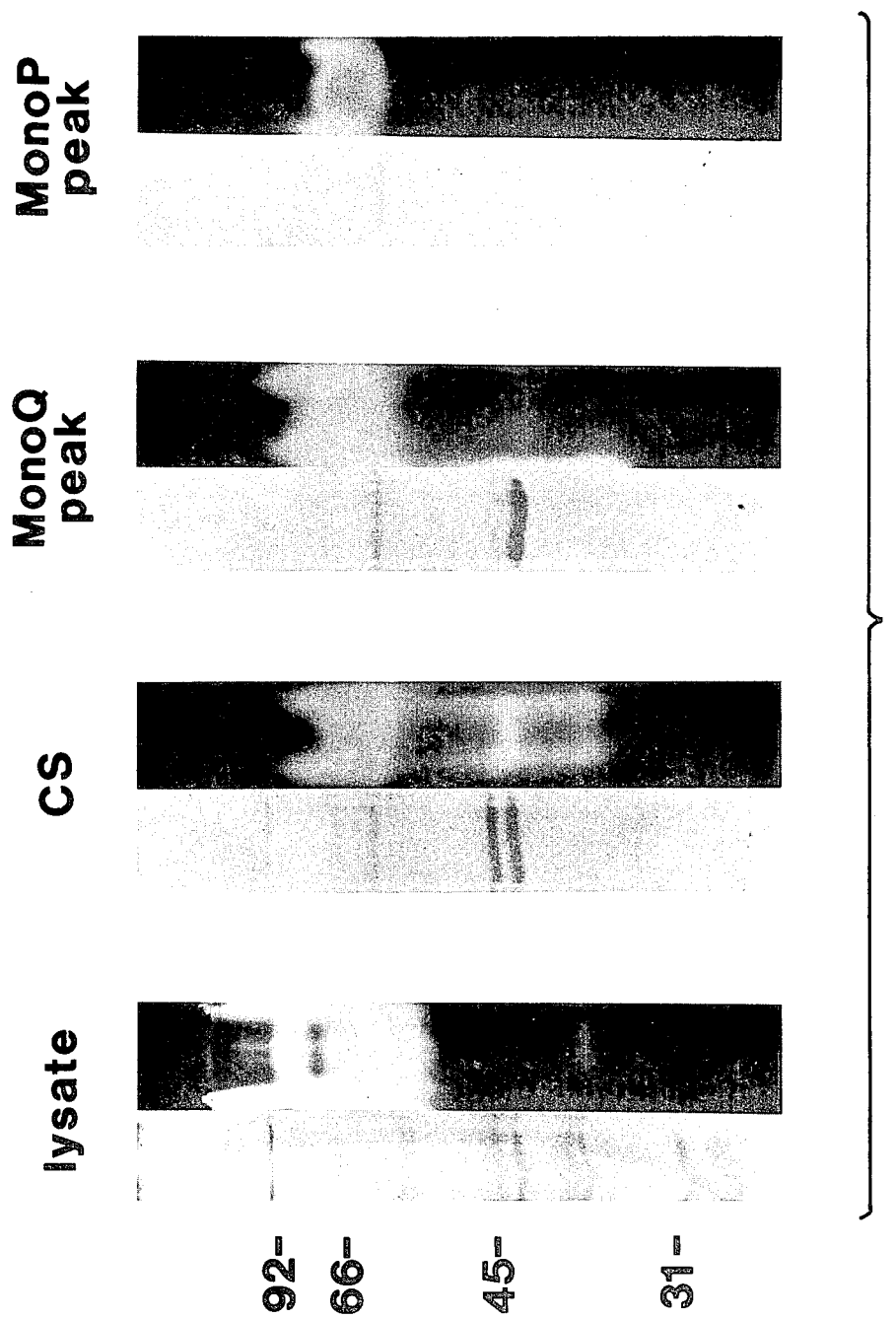
FIG. 1 is a photograph of electrophoretic gels showing ameba protein and proteinase compositions.

FIG. 1 is a photograph showing SDS-PAGE and SDS-gelatin-PAGE analysis of ameba protein and proteinase composition. Silver-stained gels of reduced enzyme samples (left) are paired with unreduced, Coomassie-stained gelatin substrate gels (right) for each fraction. CS, culture supernatant. Molecular weight markers ($M_r \times 10^{-3}$) are indicated.

Figure 2:
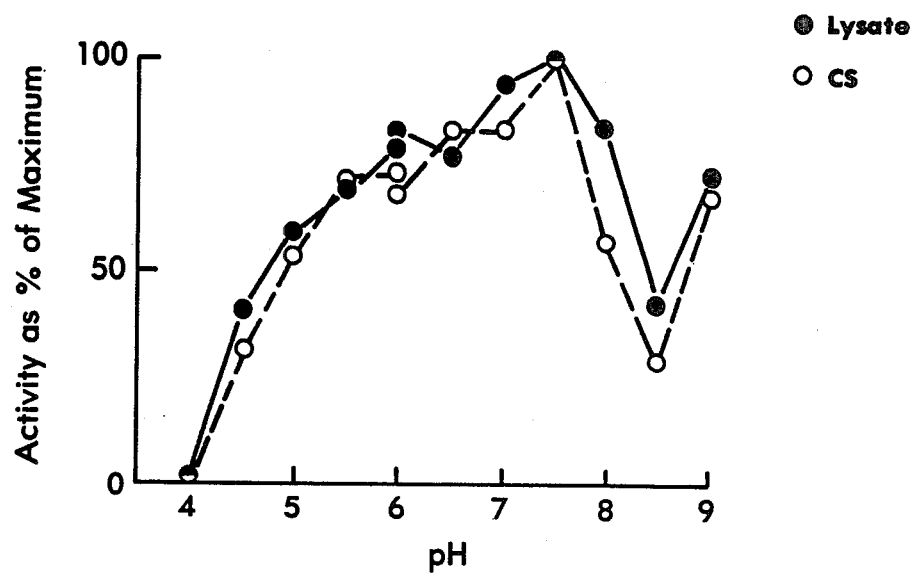
FIG. 2 is a graph showing the pH profile of culture supernatant and lysate.

FIG. 2 is a graph showing the pH profile of culture supernatant and lysate. 10 microliters of culture supernatant (CS) or lysate was assayed against Z-Arg-Arg-AMC in 100 mM acetate (pH 4-6) or 100 mM Tris (pH 6-9) buffers as described below under the heading, Materials and Methods. Results are expressed as the percentage of maximum proteolytic activity observed.

Figure 3:
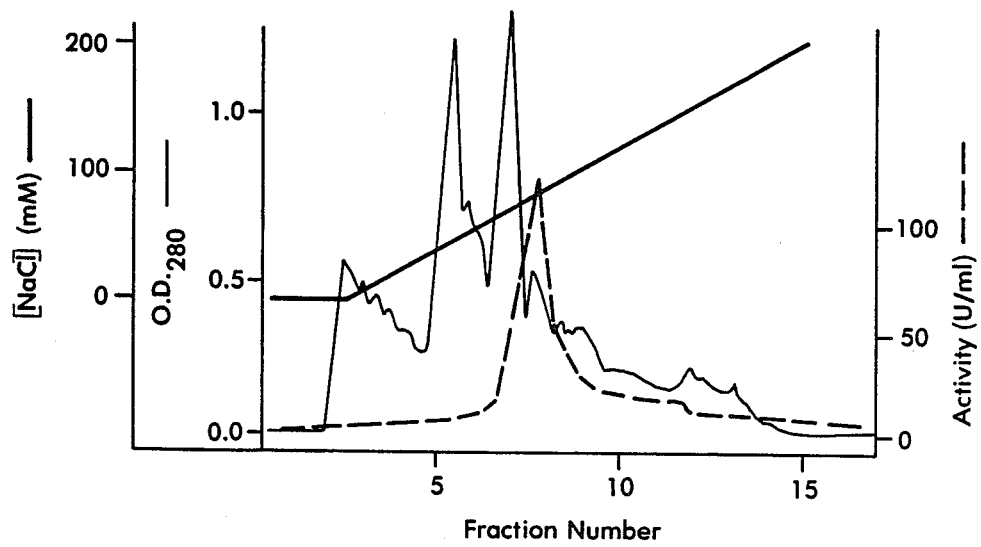
FIG. 3 is a graph showing an anion exchange (MonoQ) chromatographic analysis of culture supernatant.

FIG. 3 is a graph showing an anion exchange (MonoQ) chromatographic analysis of culture supernatant. Protein was eluted with a linear salt gradient as described in the Materials and Methods section. Proteolytic activity against Z-Arg-Arg-AMC is shown. The activity profile by Azocoll assay was identical. U, units of activity by AMC assay (micromoles substrate cleaved $\times$ liter$^{-1}$ $\times$ min$^{-1}$). O.D.$_{280}$ was measured in a 3 mm pathlength flow cell.

Figure 4:
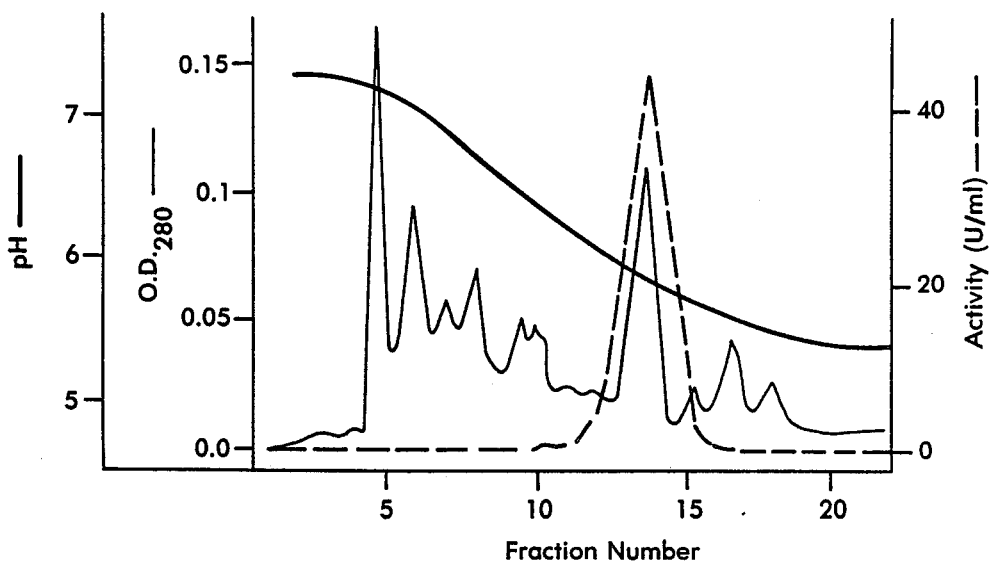
FIG. 4 is a graph illustrating chromatofocusing (MonoP) chromatography of peak activity fractions pooled from the (MonoQ) run shown in FIG. 3.

FIG. 4 is a graph illustrating chromatofocusing (MonoP) chromatography of peak fractions pooled from MonoQ purified enzyme. Protein was eluted with a pH gradient as described in the Materials and Methods section. Proteolytic activity of fractions against Z-Arg-Arg-AMC is shown. O.D.$_{280}$ was measured in a 3 mm pathlength flow cell.

Figure 5:
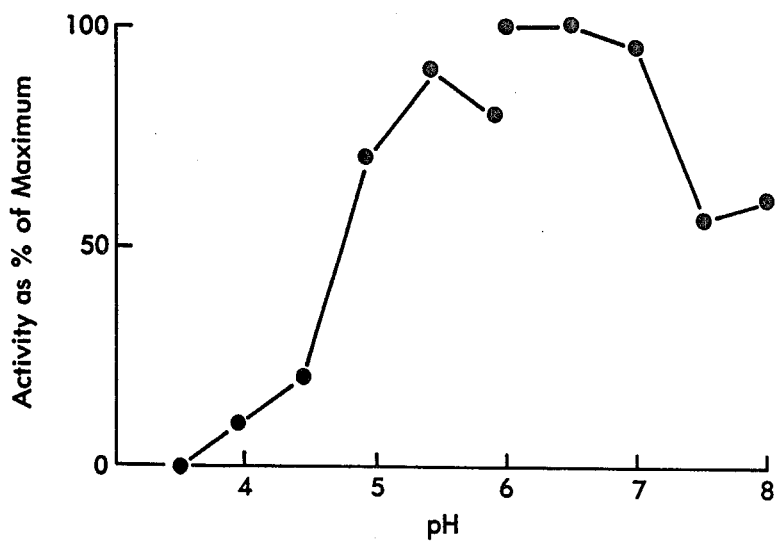
FIG. 5 is a graph showing the pH profile of MonoP purified enzyme.

FIG. 5 is a graph showing the pH profile of MonoP-purified enzyme. 10 microliters of enzyme was assayed against Z-Arg-Arg-AMC in 100 mM acetate (pH 3.5-6) or 100 mM phosphate (pH 6-8) buffers with 2 mM DTT. Results are expressed as the percentage of maximum proteolytic activity observed.

Figure 6:
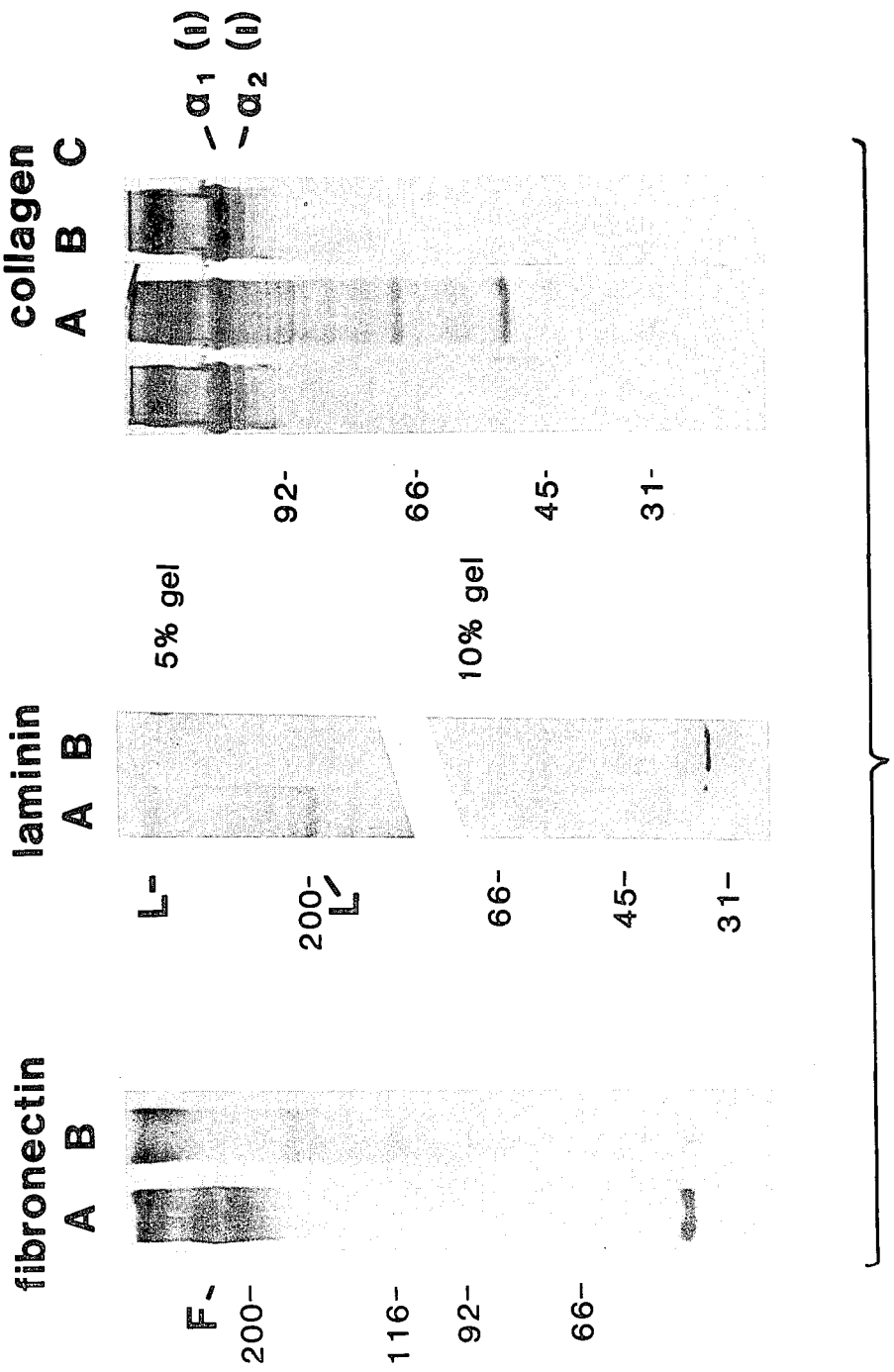
FIG. 6 is a photograph of electrophoretic gels showing connective tissue macromolecules incubated with and degraded by MonoP purified enzyme.

FIG. 6 is a photograph showing SDS-PAGE analysis of connective tissue macromolecular degradation by MonoP purified enzyme. Target species in these reduced gels are indicated: Fibronectin (F), laminin (L), and the type I collagen subunits [alpha$_1$ (I) and alpha$_2$ (I)]. Laminin was run on both 5% gels (to show laminin degradation) and 10% gels (to show cleavage products). (A) substrate alone; (B) substrate and enzyme. Collagen was also incubated with trypsin; (C), showing lack of non-specific proteolysis. Control lanes of enzyme alone had no visible staining. Molecular weight markers ($M_r \times 10^{-3}$) are indicated.

Figure 7:
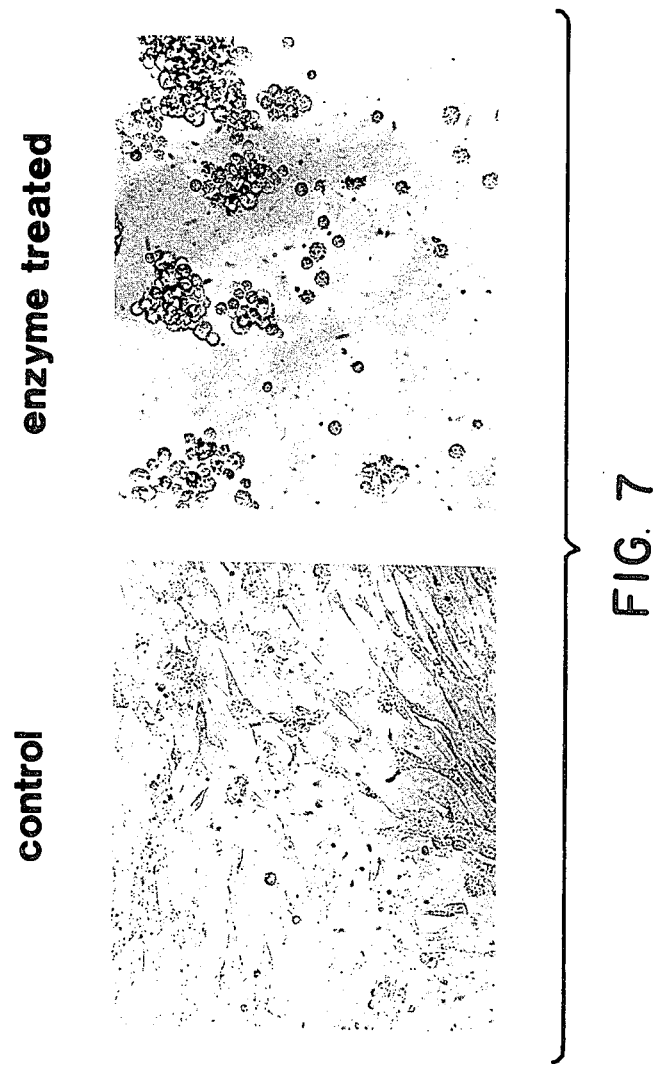
FIG. 7 is a photograph showing the cytopathic effect of a proteinase composition on baby hamster kidney (BHK) cells in culture.

FIG. 7 is a photograph showing the cytopathic effect of purified enzyme on baby hamster kidney (BHK) cells in culture. Cells rounded up and detached in wells treated with MonoP-purified enzyme (right). The same results are seen with culture supernatant. All control wells were similar to each other. Photographs were taken 90 minutes after enzyme was added.

REFERENCE LIST

The present specification refers to the following publications, each of which is expressly incorporated by reference herein.

1. Aggeler, J., J. Risch, and Z. Werb, 1981. Expression of the catalytic activity of plasminogen activator under physiologic conditions. *Biochim. Biophys. Acta.* 675: 62-68.
2. Bradford, M. M., 1976. A rapid and sensitive method for the quantitation of microgram quantities of proteins utilizing the principle of protein-dye binding. *Anal. Biochem.* 72: 248-254.
3. Castillo, M. J., K. Nukajima, M. Zimmerman, and J. C. Powers, 1979. Sensitive substrates for human leukocyte and porcine pancreatic elastase: A study of the merits of various chromophoric and fluorogenic leaving groups of assays for serine proteases. *Anal. Biochem.* 99: 53-64.
4. Diamond, L. S., 1984. Lumen dwelling protozoa: Entamoeba, Trichomonads, and Giardia. In In Vitro Cultivation of Protozoan Parasites. Jensen, J. B., editor. CRC Press, Boca Raton, FL. 65-109.
5. Engvall, E., and P. Perlmann, 1972. Enzyme-linked immunosorbent assay, ELISA, *J. Immunol.* 109: 129 (1972).
6. Gadasi, H., and D. Kobiler, 1983. *Entamoeba histolytica*: correlation between virulence and content of proteolytic enzymes. *Exp. Parasitol.* 55: 105-110.
7. Keene, W. E., and J. H. McKerrow, 1985. Isolation and characterization of the neutral thiol proteinase of virulent *Entamoeba histolytica*. *Fed. Proc.* 44: 1335.
8. Krogstad, D. J., Spencer, H. C., Jr., and G. R. Healy, 1978. Amebiasis. *The New England Journal of Medicine* 298: 262-265.
9. Laemmli, U. K., 1970. Cleavage of structural proteins during the assembly of the head of bacteriophage T4. *Nature* 227: 680-685.
10. Laug, W. B., DeClerck, Y. A. and P. A. Jones, 1983. Degradation of the subendothelial matrix by tumor cells. *Cancer Research* 43: 1827-1834.
11. Lushbaugh, W. B., Hofbauer, A. F., and F. E. Pittman, 1984. Proteinase activities of *Entamoeba histolytica* cytotoxin. *Gastroenterol.* 87: 17-27.
12. McKerrow, J. H., W. E. Keene, K. Jeong, and Z. Werb, 1983. Degradation of connective tissue matrix by larvae of *Schistosoma mansoni*. I. Degradation by cercariae as a model for initial parasite invasion of host. *Lab. Invest.* 49: 195-200.
13. McKerrow, J. H., Jones, P., Sage, H., and S. Pino-Heiss, 1985. Proteinases from invasive larvae of the trematode parasite *Schistosoma mansoni* degrade connective tissue and basement membrane macromolecules. *Biochem. J.* 231: 47-51.
14. McKerrow, J. H., S. Pino-Heiss, R. L. Lindquist, and Z. Werb, 1985. Purification and characterization of an elastinolytic proteinase secreted by cercariae of *Schistosoma mansoni*. *J. Biol. Chem.* 260: 3703-3707.
15. Unkeless, J. C., A. Tobia, L. Osowski, I. P. Quigley, D. B. Rifkin, and E. Reich, 1973. An enzymatic function associated with transformation of fibroblasts by oncogenic viruses. I. Chick embryo fibroblast cultures transformed by avian RNA tumor viruses. *J. Exp. Med.* 137: 85-111.
16. Vallee, B. L., and F. L. Hoch, 1955. Zinc, a component of yeast alcohol dehydrogenase. *Proc. Natl. Acad. Sci. USA* 41: 327.
17. Werb. Z., M. J. Banda, and P. A. Jones, 1980. Degradation of connective tissue matrices by macrophages: I. Proteolysis of elastin, glycoproteins, and collagen by proteinases isolated from macrophages. *J. Exp. Med.* 152: 1340.
18. Wray, W., T. Boulikas, V. P. Wray, and T. Hancock, 1981. Silver staining of proteins in polyacrylamide gels. *Anal. Biochem.* 118: 197-203.
19. Young, J. D. E., Young, T. M., Lu, L. P., Unkeless, J. C., and Z. A. Cohn, 1982. Characterization of a membrane pore-forming protein from *Entamoeba histolytica*. *J. Exp. Med.* 156: 1677-1690.

Definitions

In the present specification and claims, reference will be made to phrases and terms of art which are expressly defined for use herein as follows:

As used herein, "pI" means isoelectric point. A pI is determined by where a protein elutes from a chromatofocusing column.

As used herein, "FPLC" means Fast Protein Liquid Chromatography.

As used herein to describe purified neutral thiol proteinase, the term "homogeneous" means a protein contained within a single band migrating on reduced SDS-PAGE, as identified by silver staining.

As used herein, "immunogenic" means capable of provoking an immune response.

As used herein, "PBS/PS" means phosphate buffered saline, with penicillin (100 U/ml) and streptomycin (100 micrograms/ml).

As used herein, "CS" means crude culture supernatant (see section entitled "Preparation of trophozoite secretions and extracts, infra).

As used herein, "SDS-PAGE" means sodium dodecyl sulfate-polyacrylamide gel electrophoresis.

As used herein, "Azocoll" is a TM for an azo dye-linked general proteinase substrate produced by Sigma Chemical Co., P.O. Box 14508, St. Louis, MO 63178.

As used herein, "Z-Arg-Arg-AMC" means Boc-arginine-arginine-4-amino-7-methylcoumarin, a synthetic peptide substrate produced by Enzyme System Products, Livermore, Calif.

As used herein, "DTT" means DL-dithiothreitol.

As used herein, "TLCK" means tosyl-lysyl-chloromethyl ketone.

As used herein, "DMSO" means dimethylsulfoxide.

As used herein, "PMSF" means phenylmethylsulfonyl fluoride.

As used herein, "BHK" means baby hamster kidney.

As used herein, "NEM" means N-ethylmaleimide.

As used herein, "ELISA" means enzyme-linked immunosorbent assay.

As used here, "ABST" means 2,2'-azinobis(3-ethylbenzthiazoline sulfonic acid).

SUMMARY OF THE INVENTION

The present invention is a composition of matter composed essentially of a purified homogeneous thiol proteinase secreted by *Entamoeba histolytica* trophozoites. In purified homogeneous form the neutral thiol proteinase has a subunit molecular weight of about 56,000±4,000, a neutral pH optimum, and an isoelectric point of about 6 (i.e., a pI of about 6). The purified neutral thiol proteinase of the present invention can be obtained by using anion exchange and chromatofocusing Fast Protein Liquid Chromatography (FPLC) to purify the major neutral proteinase from secretions of axenically cultured *Entamoeba histolytica* trophozoites. Alternatively, the proteinase can be purified from extracts of trophozites themselves using similar protocols, as the enzyme is also found intracellularly. As disclosed below, the enzyme can be produced in large quantity by large scale production of the *Entamoeba histolytica* parasite.

The homogeneous neutral thiol proteinase of the present invention is immunogenic. It is useful as a serodiagnostic reagent for identifying the presence of antibodies in the sera of individuals exposed to *Entamoeba histolytica* trophozoites. The purified homogeneous enzyme can be used in ELISA assays or in other standard immunoassays.

DESCRIPTION OF SPECIFIC EMBODIMENTS

A neutral proteinase that is secreted by *Entamoeba histolytica* trophozoites has, for the first time, been purified to homogeneity. Detailed methods for isolating the novel neutral proteinase and purifying it to homogeneity are disclosed below in the section entitled "Experimental, Materials and Methods". Briefly, a preferred isolation and purification procedure is as follows: Axenically-grown *Entamoeba histolytica* trophozoites are harvested and incubated for three to four hours in phosphate-buffered saline (PBS). Conditioned PBS is then dialyzed, applied to an anion-exchange column, and eluted with a salt gradient. Fractions are assayed for proteolytic activity, and peak fractions are then dialyzed and applied to a chromatofocusing column. Protein is eluted with a pH gradient of 7 to 5, and fractions are checked for activity as before. The *Entamoeba histolytica* neutral proteinase elutes between pH 5.8 and 6.1.

We chose the form eluting at a pI of approximately 6 and having an approximate molecular weight of 56,000 for testing with patient sera. Proteolytic activity was assayed against both the general protease substrate Azocoll (Sigma, St. Louis, MO) and a specific peptide substrate Z-Arg-Arg-AMC (Enzyme Systems Products, Livermore, CA). Purification was monitored.

Our purified neutral proteinase is immunogenic and therefore is useful as a serodiagnostic reagent for identifying the presence of antibodies in the sera of individuals exposed to *Entamoeba histolytica* trophozoites. To illustrate the usefulness of our homogeneous neutral proteinase as a serodiagnostic reagent, we used purified neutral proteinase (having a pI of approximately 6 and a molecular weight of approximately 56,000) in an ELISA test after the methods of Engvall and Perlmann (1972). Binding of antibody from patient sera to amebic antigen was confirmed by a color reaction using horseradish peroxidase-linked goat anti-human antibody. Reactions were scored as positive or negative, depending upon development or lack of development of color following addition of HRP substrate (ABTS; Sigma). Qualitative results were then confirmed by specific absorbance readings at 414 nm on an ELISA reader (Titertek).

In running the test, 1 to 5 micrograms of purified protein was used in the ELISA to detect "amebic" antibodies in sera of patients with amebiasis versus patients with clinically similar presentations. The test was performed on ten coded samples provided by Dr. George Healy of the Centers for Disease Control, Atlanta, Ga. Using the purified neutral proteinase in the ELISA we were able to successfully identify (in a "blind" experiment) the six patients with histories of invasive amebiasis (colitis or liver abscess), while identifying as "negative" the four patients who had other diseases. We have since used this ELISA to confirm the presence of antibodies in the sera of an additional fourteen patients tested at UCSF and found seropositive by conventional tests.

In the "Experimental" section that follows we disclose preferred methods for preparing the purified neutral proteinase of the present invention. Those skilled in the art, without undue experimentation, can use our homogeneous protein composition to determine the amino acid sequence of the purified protein. Synthetic neutral proteinases substantially identical to the natural one can then be made. Alternatively, knowing the amino acid sequence, those skilled in the art can determine DNA sequences that will code for "engineered" peptides that are substantially identical to our purified neutral proteinase. Such synthesized or engineered neutral proteinases are intended to fall within the scope of the appended claims.

We have begun to characterize our purified neutral proteinase. Our test methods, and our results, are included below.

Experimental Materials and Methods

Maintenance of Cultures

Strains of *Entamoeba histolytica* can be obtained from the American Type Culture Collection (Rockville, MD) or from established cultures. We isolated the neutral thiol proteinase from axenically maintained trophozoites of the HM1:IMSS strain. *Entamoeba histolytica* cultures were maintained in TYI-S-33 medium supplemented with penicillin (100 U/ml), streptomycin (100 micrograms/ml) and 15% bovine serum (Biofluids, Inc.; Rockville, MD) following the methods of Diamond (1984).

Preparation of Trophozoite Secretions and Extracts

"Log-phase" trophozoites (72 hours after passage) were washed to remove serum, and incubated in PBS with penicillin/streptomycin for 3 hours at 37° C. Amebae maintained greater than 90% viability as judged by Trypan blue exclusion and the absence of cytosolic alcohol dehydrogenase activity (Vallee 1955) in the PBS after incubation. Amebae were centrifuged, and the resulting supernatant passed through a 0.45 micron filter. This was designated as crude culture supernatant (CS).

For extracts, trophozoites were resuspended in PBS with penicillin/streptomycin and lysed in a nitrogen cavitation bomb (Kontes Glass Co.; Vineland, N.J.) after equilibration at 30 atm ($3 \times 10^6$ N/m$^2$) for 1 hour at 40° C. After centrifugation, the supernatant of this preparation was passed through a 0.45 micron filter and designated as soluble "lysate".

The amount of protein was estimated by the method of Bradford (1976).

Purification of Proteinase Activity

To first determine how many proteolytic species were present in secretions, and their molecular weights under nonreduced conditions, 5 microliters of crude secretions and lysate were electrophoresed in 10% sodium dodecyl sulfate (SDS)-polyacrylamide gels copolymerized with 0.1% gelatin (Sigma Chemical Co.; St. Louis, MO) (McKerrow, Pino-Heiss, et al., 1985). Gels were washed to remove SDS and incubated in buffer for 6-16 hours at 37° C. After several cycles of staining and destaining, proteolytic species are seen as clear bands on a Coomassie blue-stained background. This technique, as well as SDS-polyacrylamide gel electrophoresis (PAGE) of boiled and reduced (50 mM DTT; Sigma) samples on silver stained gels (Wray, et al., 1981; Laemmli, 1970), was used to monitor purification. Molecular weights were estimated from the migration of standards (Bio-Rad; Richmond, CA).

Culture supernatant (5-10 ml at 0.5-5 mg/ml) was then dialyzed against buffer (20 mM Tris/HCl, 2 mM DTT, pH 7.5) and applied at a flow rate of 0.25 ml/min to a MonoQ anion exchange column (Pharmacia Inc., Piscataway, NJ). Protein was eluted with a linear salt gradient (20 mM Tris/HCl, 2 mM DTT, 300 mM NaCl, pH 7.5) at a flow rate of 0.5 ml/min using a GP-250 FPLC gradient programmer (Pharmacia). Fractions (1.5 ml) were collected and assayed for proteolytic activity against Azocoll, a general proteinase substrate (Sigma), and/or the synthetic peptide substrate Boc-arginine-4-amino-7-methylcoumarin (Z-Arg-Arg-AMC, Enzyme System Products; Livermore, CA), which has been shown to be a substrate for the major neutral proteinase (Keene and McKerrow 1985).

Fractions of peak activity from the anion exchange column were pooled and dialyzed overnight against buffer (25 mM bis-Tris, 2 mM DTT, pH 7.1) and applied to a MonoP chromatofocusing column at a flow rate of 0.25 ml/min. Typically, about 3 ml at 0.5 mg/ml were injected. Protein was eluted at a flow rate of 0.5 ml/min over a pH gradient of 7-5 formed with 10% Polybuffer 74, pH 5. (Polybuffer 74 is the Trademark of Pharmacia Inc., 800 Centennial Avenue, Piscataway, NJ 08854 for an amphoteric chromatofocusing buffer.) The gradient was generated with the GP-250 gradient programmer and continuously monitored with a pH meter and flow cell. Fractions were collected and checked for activity as described above.

2 mM DTT was maintained throughout as it enhanced activity 2-4-fold in assays and prolonged stability of the enzyme during storage. Even so, as much as 25% of the activity was lost per day in storage at −20° C. Storage at −70° C. or 4° C. gave similar results.

Assays for Proteolytic Activity

All assays were performed in 100 mM Tris/HCl, 2 mM DTT, pH 7.4 unless otherwise noted.

Azocollytic activity was measured by incubation of 3 mg Azocoll with 10-100 microliters of enzyme (1 ml reaction volume) for 3-16 hours at 37° C. The tubes were then vortexed, microfuged, and the amount of degradation determined from the absorbance of the supernatant at 540 nm ($A_{540}$). Control tubes were incubated without enzyme; bovine trypsin (5 micrograms; Sigma) was used to determine the total available substrate.

The Z-Arg-Arg-AMC assay is based on the fluorescence of the cleaved AMC group at 460 nm when excited at 380 nm (Castillo, et al, 1979). Enzyme samples (5-25 microliters) were added to a 4 micromolar solution of Z-Arg-Arg-AMC in buffer to a total volume of 2 ml. The rate of substrate hydrolysis at room temperature was determined from the rate of increase of fluorescence, monitored on a continuously recording spectrofluorometer (Aminco SPF-500; American Instrument Co., Silver Spring, MD). The scale was calibrated with a stock solution of 1.3 micromolar AMC (Sigma).

Degradation of Fibronectin, Laminin, Elastin, and Type 1 Collagen 40 microgram aliquots of fibronectin (Bethesda Research Laboratories (BRL); Bethesda, MD), laminin (BRL), or type 1 collagen ("Vitrogen 100"), (Vitrogen 100 is the Trademark of Collagen Corp., Palo Alto, CA for a sterile solution of purified bovine dermal type I collagen), diluted to 1 mg/ml in buffer with 150 mM NaCl, were mixed with 40 microliters of MonoP purified enzyme or 10-20 microliters of culture supernatant. Volumes were brought to 80 microliters with 100 mM Tris, pH 7.2, and DTT was added to a final concentration of 2 mM. Samples were incubated for 3.5 hours (fibronectin and collagen) or 20 hours (laminin) at 37° C. along with matched amounts of substrate or enzyme alone as controls. Collagen was also incubated with 0.5 micrograms of TPCK trypsin (trypsin with tosyl-phenylalanine-chloromethyl-ketone to inhibit any contaminating chymotrypsin, (Worthington Biochemical Corp.; Freehold, NJ) to assay for non-specific cleavage.

Reactions were terminated with 2x sample buffer, and analyzed by SDS-PAGE (laminin with 5% and 10% gels; fibronectin with 7% gels; collagen with 10% gels) for evidence of degradation; 80 microliters was loaded into each lane.

Elastase activity was assayed as described by McKerrow, Pino-Heiss, et al. (1985). Briefly, 200 micrograms of NaB[$^3$H]$_4$-labeled elastin (Elastin Corp.; St. Louis, MO) was incubated with 100 microliters of culture supernatant and 100 microliters of MonoP purified enzyme in buffer (reaction volume: 300 microliters) for 19 hours at 37° C. Total available substrate was determined by digest with pancreatic elastase (Sigma).

Plasminogen Activator Assay

Plasminogen activator activity was determined by the method of Unkeless, et al. (1973) as modified by Aggeler, et al. (1981). Briefly, 24-well plates were coated with [$^{125}$I]-labeled fibrinogen, and incubated with calf serum for two hours at 37° C. to convert fibrinogen to fibrin. Plasminogen (280 ng; final concentration, 6 nM) was added in 50 mM Tris/HCl (pH 7.8) with 100 microliters of culture supernatant or amebic lysate or 50 microliters of MonoP-purified enzyme, to a final volume of 0.5 ml. Controls were incubated without plasminogen added. Aliquots of supernatant (50 microliters) from quadruplicate wells were counted in a gamma counter (Auto-Gamma 500; Packard Instrument Corp.; Downer's Grove, IL). Total available fibrin was determined by trypsin digest. Urokinase (10 ploug units, Calbiochem; La Jolla, CA) was assayed for comparison. Results were expressed as the percentage of total available fibrin degraded less the percentage degraded by the corresponding plasminogen-free control.

Effects of Inhibitors

Inhibitors were preincubated with the enzyme at the indicated concentrations (See Table 1) for 20 minutes at ambient temperature; substrate was then added and proteolytic activity assayed against Z-Arg-Arg-AMC. All inhibitors were obtained from Sigma except pepstatin A (Transformation Research, Inc., Farminham, MA) and bovine serum (Biofluids). TLCK was prepared as a stock solution in dimethyl sulfoxide (DMSO). Phenlylmethylsulfonyl fluoride (PMSF), pepstatin A, and 1,10-phenanthroline stock solutions were made up in ethanol. An equal volume of DMSO or ethanol alone was tested with enzynme and inhibition was calculated relative to the appropriate solvent control.

pH profile

Crude or chromatography-purified enzyme was assayed for proteolytic activity against Z-Arg-Arg-AMC as described above. Acetate buffer (100 mM) was used for pH 4-6, 100 mM phosphate buffer for pH 6.0-8.0, and 100 mM Tris for pH 6.0-10.0. All buffers included 2 mM DTT.

Assay for Cytopathic Effects

Confluent monolayers of baby hamster kidney (BHK) cells (obtained from the University of California at San Francisco's Cell Culture Facility), grown in 24-well tissue culture plates in Dulbecco's modified Eagle's (DME-H21) supplemented with 2 mM glutamine, penicillin/streptomycin, and 6% fetal bovine serum), were washed to remove serum and incubated at 37° C. with 200 microliters of culture supernatant or 400 microliters of MonoP purified enzyme (Medium was added to a total volume of 1 ml/well). Duplicate wells were compared with control wells of DME-H21 diluted with matched amounts of PBS or buffer. Cells were examined with an inverted microscope for evidence of cytopathic effects (cell rounding and detachment) over the next three hours.

Results

Activity of Unpurified Enzyme

Both lysate and culture supernatant had activity against Azocoll and the Z-Arg-Arg-AMC peptide substrate. Lysate from HM-1 trophozoites had twice as much proteolytic activity against the Azocoll substrate as that from the same number of trophozoites of another axenized strain of Entamoeba histolytica, the HK-9 strain. Culture supernatant from HM-1 amebae was 5 times more active than that from an equal number of HK-9 trophozoites. The more active HM-1 strain was therefore used for the subsequent purification and characterization of neutral proteinase activity.

SDS-PAGE and SDS-gelatin-PAGE showed that although both lysate and culture supernatant were complex mixtures, the major proteolytic activity was found at $M_r$ 50,000 to 70,000 (See FIG. 1). Tested over a pH range from 4-10, both lysate and culture supernatant had a peak of proteolytic activity at pH 7.5 (See FIG. 2). This activity was completely inhibited by NEM, iodoacetate, and TLCK, but not affected by PMSF, EDTA, pepstatin, or 1,10 phenanthroline at the concentrations tested (See Table I).

Culture supernatant (100 microliters) activated plasminogen sufficient to degrade 19% of the available fibrin in 3 hours. The same amount of lysate degraded 25% of available fibrin, and 10 ploug units of urokinase degraded 38%.

Our results with unpurified material suggested that the major proteinase of Entamoeba histolytica was a thiol enzyme that was secreted by trophozoites and that would be active in the neutral pH environment of the host. Our subsequent work was aimed at purifying and further characterizing this activity. Insofar as we observed no significant qualitative difference between the proteolytic activities of lysate and culture supernatant, and because there were considerably fewer major proteins in culture supernatant (See FIG. 1), we chose the latter as the starting material for further purification.

Chromatographic Purification and Activity of Purified Fractions

Activity eluted from the MonoQ anion-exchange column as a single peak at a salt concentration of 60-80 mM (see FIG. 4). When peak fractions were pooled and applied to the MonoP chromatofocusing column, activity eluted in a single peak at pH 5.9-6.2 (see FIG. 4). SDS-PAGE indicated a subunit molecular weight of 56,000±4,000 (See FIG. 1).

In a typical preparation, specific activity was increased 10-fold over that of culture supernatant, with 19% of total activity recovered (See Table II).

When assayed in phosphate buffer, MonoP-purified enzyme had maximal activity against Z-Arg-Arg-AMC at pH 6-7 (See FIG. 5). In Tris buffer, there was a broader peak from pH 7-9.5 (data not shown). The proteolytic activity of purified enzyme was completely inhibited by NEM, iodoacetate, leupeptin, alpha$_1$-proteinase inhibitor, TLCK, and serum at the concentrations tested (See Test I).

Analysis of SDS-PAGE indicated that the purified neutral thiol proteinase was able to degrade purified laminin, fibronectin, and type I collagen (See FIG. 6). Collagen was cleaved into many fragments; the characteristic cleavage pattern of bacterial collagenase, with major fragments of $M_r$ 75,000, 50,000 and 25,000, was not apparent. Culture supernatant also degraded these macromolecules (not shown).

MonoP-purified enzyme (50 microliters, about 1 microgram) activated plasminogen sufficient to degrade 3.4% of the available fibrin in 2.5 hours.

There was no degradation of [$^3$H]-elastin by culture supernatant or purified enzyme.

Cytotopathic Effects

Both culture supernatant and purified enzyme caused marked effect on cell adhesion, which was evident within 45 minutes. At 2 hours, more than 95% of the cells had rounded up and detached (See FIG. 7). In control wells, less than 25% of the cells had detached. However, no lysis or osmotic damage to cells was observed. Detached cells, when washed and replated, reattached and exhibited normal morphology.

Discussion

We have purified to homogeneity a neutral proteinase that is secreted by Entamoeba histolytica trophozoites and can also be identified in the soluble fraction of trophozoite lysate (Keene, et al., 1985). Because of its inhibition profile and potentiation by dithiothreitol, we believe the enzyme is a thiol proteinase. Our thiol proteinase is active against a synthetic peptide substrate with arginine at P-1 and P-2. The homogeneous enzyme has a subunit molecular weight of about 56,000 (by SDS- PAGE) and an approximate pI of 6 (by chromatofocusing).

The neutral thiol proteinase is important in the pathogenesis of extraintestinal amebiasis. This was first suggested by our observations that it is secreted by trophozoites and active at neutral pH. Furthermore, HM-1 strain trophozoites secrete more of this proteinase than the less virulent HK-9 stain. Other investigators have also correlated strain virulence with proteolytic activity.

The results of assays of crude and purified enzyme against an in vitro model of extracellular matrix, as well as against purified type I collagen, laminin, and fibronectin, suggest how this enzyme may play a key role in both invasion and tissue damage by trophozoites. Gadasi and Kobiler (1983) showed that crude lysate from HM-1 trophozoites degraded fibronectin. Our results with purified enzyme confirm this finding and identify the proteinase responsible for this activity. Furthermore, we have shown that this enzyme cleaves laminin, which plays a critical role in anchoring epithelial cells to underlying basal lamina, as well as in maintaining the structural integrity of the basement membrane.

It has been proposed that proteinase are involved in the observed cytopathic effects of virulent trophozoites on cells in culture (Lushbaugh, et al., 1984). Our demonstration of cell detachment and rounding up after exposure to the purified enzyme supports this hypothesis and probably reflects the ability of the enzyme to degrade anchoring proteins. Some investigators have used the term "cytophatic effect" to describe this cell detachment. This phenomenon, however, must be distinguished from cell lysis or osmotis damage, which we did not observe. Lysis per se may require the activity of other cytotoxic factors, such as the amebapore (Young, et al., 1982). Nevertheless, proteinase-mediated detachment of epithelia cells from the bowel mucosa may be an important pathogenatic mechanism in amebiasis.

In addition to degrading host extracellular matrix and basement membrane macromolecules, the enzyme we have purified is a plasminogen activator. We tested for this activity because the enzyme cleaved synthetic peptides with arginine at P-1, as do other plasminogen activators. Therefore, aside from directly mediating tissue damage, the amebic enzyme may potentiate host proteinases by activating plasmin. Plasmin can then amplify its own activation, as well as activate latent tissue collagenases.

TABLES

TABLE I

INHIBITION OF MONO P PURIFIED ENZYME

| Inhibitor | Final Concentration | Activity as % of control (without inhibitor) | |
|---|---|---|---|
| | | Culture Supernatant* | Mono P-purified Enzyme** |
| N—ethylmaleimide (NEM) | 5 mM | 5 | 0 |
| iodoacetate | 3 mM | 0 | 0 |
| leupeptin | 10 microM | 68 | 16 |
| | 50 microM | N.D. | 0 |
| alpha₁-proteinase inhibitor | 100 microgram/ml | 58 | 0 |
| tosyl-lysyl-chloromethyl ketone (TLCK) | 0.1 mM | 0 | 0 |
| aprotinin (trasylol) | 100 microgram/ml | 100 | 100 |
| ethylenediaminetetracetic acid (EDTA) | 10 mM | 100 | 100 |
| phenylmethylsulfonyl fluoride (PMSF) | 2 mM | 100 | 100 |
| 1,10-phenanthroline | 2 mM | 100 | 100 |
| pepstatin A | 100 microgram/ml | 100 | 100 |
| bovine serum | 0.5% (v/v) | 0 | 0 |
| soybean trypsin inhibitor (SBTI) | 100 microgram/ml | 100 | 100 |

*By Z—Arg—Arg—AMC assay, except PMSF and serum, which were by Azocoll assay.
**By Azocoll assay.
N.D., not determined

TABLE II

PURIFICATION TABLE OF THE NEUTRAL THIOL PROTEINASE

| Step | Total Protein (mg) | Specific Activity (U/mg) | Enrichment (-fold) | Total Activity (U) | Recovery (%) |
|---|---|---|---|---|---|
| culture supernatant | 4.7 | 57 | 1 | 268 | 100 |
| anion exchange (MonoQ) | 1.2* | 130* | 2* | 220** | 82** |
| Chromato-focusing (MonoP) | .022* | 590* | 10* | 50** | 19** |

*for peak fractions
**total for all fractions recovered.
Values are for a representative purification, assayed for activity against Z—Arg—Arg—AMC. U, units of activity (micromoles AMC cleaved × liter⁻¹ · min⁻¹).

SUMMARY

From the foregoing description, one of ordinary skill in the art can easily ascertain that the present invention provides a novel homogeneous thiol proteinase that in nature is secreted by Entamoeba histolytica trophozoites. In isolated, homogeneous from the Entamoeba histolytica thiol proteinase is immunogenic and therefore useful as a serodiagnostic reagent for detecting the presence of antibodies to the protozoan parasite known to cause amebiasis.

Without departing from the spirit and scope of this invention, one of ordinary skill can make various changes and modifications to the invention to adapt it to various usages and conditions. Alternative procedures can be used to purify this enzyme from secretions or lysate of Entomoeba histolytica trophozoites. As such, these changes and modifications are properly, equitably, and intended to be, within the full range of equivalence of the following claims.

What is claimed is:

1. A proteinaceous composition consisting essentially of a homogeneous neutral proteinase secreted by Entamoeba histolytica trophozoites wherein said proteinase has a subunit molecular weight of 56,000±4,000 by SDS-PAGE, a neutral pH optimum, and an isoelectric point of about 6.

2. A synthetic proteinaceous composition consisting of a protein that is substantially identical to a homogeneous neutral proteinase secreted by Entamoeba histolytica trophozoites wherein said homogeneous neutral proteinase has a subunit molecular weight of 56,000±4,000 by SDS-PAGE, a neutral pH optimum, and an isoelectric point of about 6.

3. An engineered proteinaceous composition produced by a recombinant host cell wherein said composition is substantially identical to a homogeneous neutral proteinase secreted by Entamoeba histolytica trophozoites, said homogeneous neutral proteinase having a subunit molecular weight of 56,000±4,000 by SDS-PAGE, a neutral pH optimum, and an isoelectric point of about 6.

* * * * *